(12) United States Patent
Crofford

(10) Patent No.: US 7,713,284 B2
(45) Date of Patent: May 11, 2010

(54) SELF-OPENING SKIN STAPLE

(76) Inventor: Theodore W. Crofford, 6863 Lohantan Dr., Fort Worth, TX (US) 76132

( * ) Notice: Subject to any disclaimer, the term of this patent is extended or adjusted under 35 U.S.C. 154(b) by 386 days.

(21) Appl. No.: 11/900,720

(22) Filed: Sep. 13, 2007

(65) Prior Publication Data

US 2008/0077144 A1   Mar. 27, 2008

Related U.S. Application Data

(60) Provisional application No. 60/844,270, filed on Sep. 13, 2006.

(51) Int. Cl.
*A61D 1/00* (2006.01)
(52) U.S. Cl. ....................... 606/219; 606/151
(58) Field of Classification Search ............. 606/60–75, 606/151, 157, 219–221; 411/457
See application file for complete search history.

(56) References Cited

U.S. PATENT DOCUMENTS

| 2,745,308 | A | | 3/1955 | Gisondi |
| 3,515,194 | A | | 6/1970 | Hirst et al. |
| 4,317,451 | A | | 3/1982 | Cerwin et al. |
| 4,444,181 | A | * | 4/1984 | Wevers et al. ................. 606/75 |
| 4,531,522 | A | | 7/1985 | Bedi et al. |
| 4,637,765 | A | | 1/1987 | Omata |
| 5,236,440 | A | * | 8/1993 | Hlavacek ................... 606/219 |
| 5,423,857 | A | * | 6/1995 | Rosenman et al. .......... 606/219 |
| 5,478,353 | A | | 12/1995 | Yoon |
| 5,567,098 | A | | 10/1996 | Gordon |
| 5,584,856 | A | | 12/1996 | Jameel et al. |
| 5,720,753 | A | | 2/1998 | Sander et al. |
| 5,968,078 | A | | 10/1999 | Grotz |
| 5,993,476 | A | * | 11/1999 | Groiso ....................... 606/219 |
| 6,210,419 | B1 | * | 4/2001 | Mayenberger et al. ...... 606/158 |
| 6,695,883 | B2 | | 2/2004 | Crofford |
| 6,969,398 | B2 | | 11/2005 | Stevens et al. |
| 7,104,995 | B2 | | 9/2006 | Crofford |
| 2006/0111721 | A1 | | 5/2006 | Puricelli et al. |
| 2006/0241619 | A1 | | 10/2006 | Cerundolo |

* cited by examiner

Primary Examiner—(Jackie) Tan-Uyen T. Ho
Assistant Examiner—Melanie Tyson
(74) Attorney, Agent, or Firm—Klemchuk Kubasta LLP; Darin M. Klemchuk

(57) ABSTRACT

A tissue closure apparatus having a collar, a pair of elastically deformable legs, and a flexible adjustment member is provided. The collar includes a collar wall defining a passage therethrough, along which are disposed a plurality of teeth extending outward into the passage. A pair of elastically deformable legs is connected to the collar, and each leg includes a lateral portion adjacent the collar and an engagement portion connected to the lateral portion. A flexible adjustment member is connected to the engagement portion of at least one of the elastically deformable legs. The flexible adjustment member is disposed within the passage of the collar and includes a plurality of teeth to engage the plurality of teeth of the collar.

1 Claim, 1 Drawing Sheet

SELF-OPENING SKIN STAPLE

CROSS-REFERENCE TO RELATED APPLICATIONS

This application claims the benefit of and priority to U.S. Provisional Application No. 60/844,270, filed Sep. 13, 2006, which is hereby incorporated by reference.

BACKGROUND OF THE INVENTION

1. Field of the Invention

The present invention relates generally to wound closure devices and in particular to a self-opening skin staple used to close wounds on a patient.

2. Description of Related Art

Existing skin staples, when engaged to the skin of a patient, are proximate the upper surface of the patient's skin and require a special extraction tool to extract the staple. Extraction of these staples requires that the tool be placed under the staple so that the legs of the staple can be forced open. This operation frequently causes significant pain to patients who are often already experiencing pain due to a recovering wound proximate the staple. A need therefore exists for an apparatus that has the wound closure abilities of a traditional skin staple, yet reduces the pain caused to a patient upon removal of the device.

BRIEF SUMMARY OF THE INVENTION

The problems presented by existing skin staples and other closure methods are solved by the systems and methods of the present invention. A tissue closure apparatus is provided according to an embodiment of the present invention. The apparatus includes a collar having a collar wall defining a passage therethrough. The collar wall includes an inner surface adjacent the passage, and the inner surface includes a plurality of teeth extending outward into the passage. A pair of elastically deformable legs is connected to the collar, and each leg includes a lateral portion adjacent the collar and an engagement portion connected to the lateral portion. A flexible adjustment member is connected to the engagement portion of at least one of the elastically deformable legs. The flexible adjustment member is disposed within the passage of the collar and includes a plurality of teeth to engage the plurality of teeth of the collar. The flexible adjustment member is capable of being pulled through the passage such that the at least one of the elastically deformable legs is moved from an open position to an engaged position. The teeth of the flexible adjustment member lockingly engage the teeth of the collar such that the elastically deformable leg remains in the engaged positioned until selectively released.

Other objects, features, and advantages of the present invention will become apparent with reference to the drawings and detailed description that follow.

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
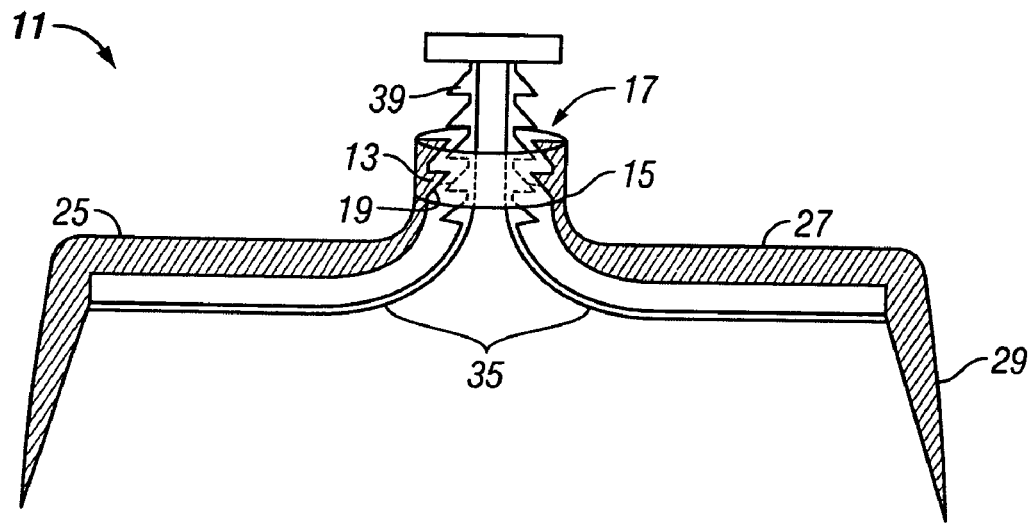
FIG. 1 illustrates a tissue closure apparatus according to an embodiment of the present invention, the apparatus being shown in an open position.
Figure 2:
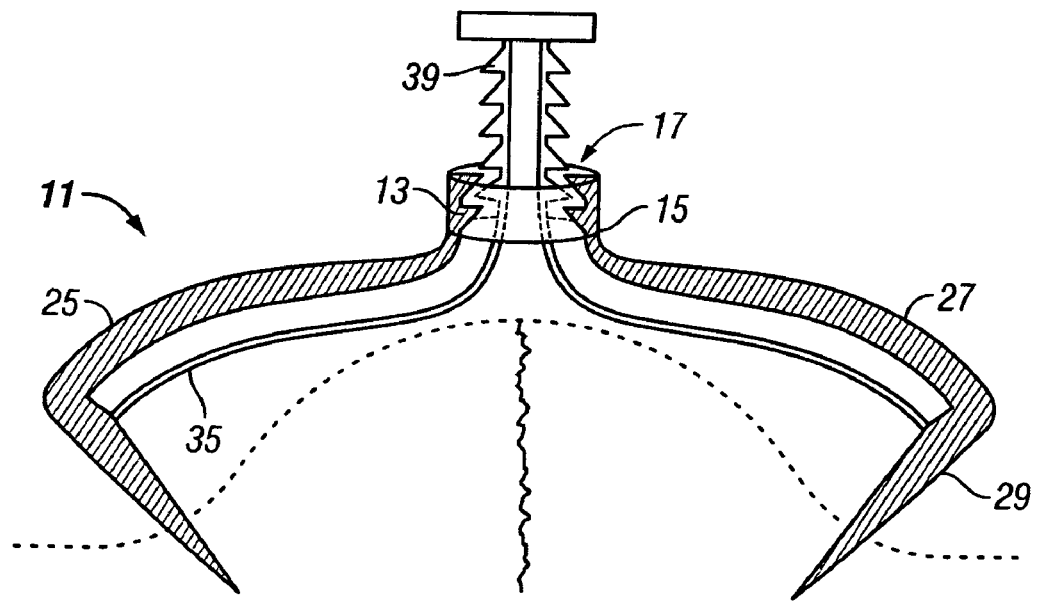
FIG. 2 depicts the tissue closure apparatus of FIG. 1 in an engaged position.

Referring to FIGS. 1 and 2, a tissue closure apparatus 11 of the present invention includes a collar 13 having a collar wall 15 defining a passage 17 therethrough. The collar wall 15 includes an inner surface adjacent the passage 17, and a plurality of teeth 19 are disposed on the inner surface of the collar wall 15. The teeth 19 extend outward from the inner surface into the passage 17.

The tissue closure apparatus 11 further includes a pair of elastically deformable legs 25 connected to the collar 13, each leg 25 having a lateral portion 27 adjacent the collar and an engagement portion 29 connected to the lateral portion. The connection between the engagement portion 29 and the lateral portion 27 may be a pivotal or hinge connection. If so, a living hinge formed from the same material as the lateral portion 27 and the engagement portion 29 would be preferable, however, a mechanical hinge could also be employed. It should be noted; however, that a pivotal or hinge-type connection between the portions of the leg 25 is not required. Instead, the legs 25 may be configured to rotate relative to the collar 13 due to a pivotal or hinge-type connection with the collar, or movement of the engagement portion 29 relative to the collar 13 may be provided solely by the elasticity of the legs themselves.

The tissue closure apparatus 11 further includes a flexible adjustment member 35 connected to the engagement portion of at least one of the elastically deformable legs 25. The flexible adjustment member 35 is further disposed within the passage 17 of the collar 13 and includes a plurality of teeth 39 to engage the plurality of teeth 19 of the collar 13. When the end of the flexible adjustment member opposite the end connected to the leg is pulled, the flexible adjustment member slides through the passage and causes the at least one of the elastically deformable legs to move from an open position (FIG. 1) to an engaged position (FIG. 2). As the flexible adjustment member slides through the passage, the teeth of the flexible adjustment member lockingly engage the teeth of the collar such that the elastically deformable leg remains in the engaged positioned.

The movement of the legs from the open position to the engaged position is preferably accomplished when the tissue closure apparatus 11 is placed above and proximate to the tissue of the patient in the area of a wound to be closed. As the legs engage the tissue, the tissue is penetrated by the engagement portion of each leg and a force is exerted by the legs on the tissue to close the wound to which the tissue closure apparatus 11 is applied. When it is desired to remove the tissue closure apparatus 11 (following healing of the wound), each leg and adjustment member may by easily cut just below the collar, which releases the force applied by the adjustment member to each leg. Since the legs were only elastically deformed, the legs will return to a shape and position similar to that held prior to installation of the tissue closure apparatus 11. Each leg can then be easily removed with minimal discomfort to the patient. The time required for each leg to elastically rebound may be selected based on the material used for the legs.

It should be apparent from the foregoing that an invention having significant advantages has been provided. While the invention is shown in only a few of its forms, it is not just limited but is susceptible to various changes and modifications without departing from the spirit thereof.

I claim:

1. A tissue closure apparatus comprising:

a collar having a collar wall defining a passage therethrough, the collar wall having an inner surface adjacent the passage, the inner surface having a plurality of teeth extending outward into the passage;

a pair of elastically deformable legs connected to the collar, each leg having a lateral portion adjacent the collar and an engagement portion connected to the lateral portion;

a flexible adjustment member connected to the engagement portion of at least one of the elastically deformable legs, the flexible adjustment member being disposed within the passage of the collar and having a plurality of teeth to engage the plurality of teeth of the collar; and wherein the flexible adjustment member is capable of being pulled through the passage such that the at least one of the elastically deformable legs is moved from an open position to an engaged position, the teeth of the flexible adjustment member lockingly engaging the teeth of the collar such that the elastically deformable leg remains in the engaged positioned until selectively released.

* * * * *